(12) United States Patent
Van Egmond et al.

(10) Patent No.: US 10,632,265 B2
(45) Date of Patent: Apr. 28, 2020

(54) AEROSOL OR SPRAY DEVICE, SPRAY NOZZLE UNIT AND METHOD OF MANUFACTURING THE SAME

(71) Applicant: Medspray B.V., Enschede (NL)

(72) Inventors: Henri Van Egmond, Emmerich am Rhein (DE); Wilhelmus Petrus Johannes De Kruijf, Enschede (NL); Wietze Nijdam, Enschede (NL); Jeroen Mathijn Wissink, Enschede (NL); Cornelis Johannes Maria Van Rijn, Amsterdam (NL)

(73) Assignee: Medspray B.V., Enschede (NL)

( * ) Notice: Subject to any disclaimer, the term of this patent is extended or adjusted under 35 U.S.C. 154(b) by 0 days.

(21) Appl. No.: 15/320,371

(22) PCT Filed: Jun. 19, 2015

(86) PCT No.: PCT/NL2015/050455
§ 371 (c)(1),
(2) Date: Dec. 20, 2016

(87) PCT Pub. No.: WO2015/194962
PCT Pub. Date: Dec. 23, 2015

(65) Prior Publication Data
US 2017/0281880 A1    Oct. 5, 2017

(30) Foreign Application Priority Data

Jun. 20, 2014   (NL) ...................................... 2013044

(51) Int. Cl.
*A61M 11/00*   (2006.01)
*B05B 15/40*   (2018.01)
(Continued)

(52) U.S. Cl.
CPC ......... *A61M 11/007* (2014.02); *A61M 11/003* (2014.02); *A61M 35/00* (2013.01);
(Continued)

(58) Field of Classification Search
CPC ................ A61M 11/007; A61M 35/00; A61M 2207/00; B05B 1/169; B05B 1/14; B05B 15/008
See application file for complete search history.

(56) References Cited

U.S. PATENT DOCUMENTS 1,346,877 A * 7/1920 Burroughs ............... B29D 1/00
156/69
1,645,893 A * 10/1927 Bucknam .............. F23D 14/465
239/533.1
(Continued)

FOREIGN PATENT DOCUMENTS

CN     101104463 A    1/2008
FR       2851483 A1    8/2004

*Primary Examiner* — Viet Le
(74) *Attorney, Agent, or Firm* — Hoffman & Baron, LLP

(57) ABSTRACT

A method for manufacturing an spray device includes assembling at least one spray nozzle plate into a thermoplastic holder, while controlling the temperature of the spray nozzle plate and/or the holder and as a result at least locally plastically deforming the holder permanently. After the thermoplastic deformation of a seat of the holder, a diameter of the seat of the holder upstream of the spray nozzle plate exceeds a diameter of the seat of the holder downstream of the nozzle plate. The thermoplastic holder may have a tapered seat, where the smallest cross section of the tapered seat is smaller than the spray nozzle plate, where a widest side of the tapered seat is pointing towards a supply side of the liquid.

13 Claims, 12 Drawing Sheets

(51) Int. Cl.
*B05B 1/14* (2006.01)
*A61M 35/00* (2006.01)
*B05B 1/16* (2006.01)

(52) U.S. Cl.
CPC ............... *B05B 1/14* (2013.01); *B05B 1/169* (2013.01); *B05B 15/40* (2018.02); *A61M 11/006* (2014.02); *A61M 2207/00* (2013.01)

(56) References Cited

U.S. PATENT DOCUMENTS

| | | | | |
|---|---|---|---|---|
| 1,826,776 A | * | 10/1931 | Gunther | F23D 11/103 239/11 |
| 1,914,072 A | * | 6/1933 | Boylston | F16L 55/02718 181/239 |
| 2,289,494 A | * | 7/1942 | Hadley | F23D 11/24 138/37 |
| 2,517,482 A | * | 8/1950 | Hall | A61M 15/0028 128/203.15 |
| 2,646,113 A | * | 7/1953 | Tavener | F23D 14/00 239/590.5 |
| 2,882,993 A | * | 4/1959 | Murty | F16L 55/02718 181/281 |
| 3,010,910 A | * | 11/1961 | Gauchard | A61M 11/06 128/200.21 |
| 3,066,669 A | * | 12/1962 | De Melfy | A61M 11/06 128/200.18 |
| 3,120,348 A | * | 2/1964 | O'Donnell | B05B 1/3436 239/490 |
| 3,176,921 A | * | 4/1965 | De Voe | F23D 1/005 239/124 |
| 3,357,047 A | * | 12/1967 | Keil | B60C 11/18 239/596 |
| 3,491,181 A | * | 1/1970 | Keil | B60C 11/18 264/219 |
| 3,518,339 A | * | 6/1970 | Goff | B29C 65/542 264/249 |
| 3,532,128 A | * | 10/1970 | Rosales | F15D 1/02 138/45 |
| 3,545,492 A | * | 12/1970 | Scheid, Jr. | F16L 55/02718 138/42 |
| RE27,736 E | * | 8/1973 | Muhlner et al. | B29C 57/025 264/249 |
| 3,831,350 A | * | 8/1974 | Gilles | F15D 1/02 138/37 |
| 3,867,092 A | * | 2/1975 | Sage | F23D 11/102 239/431 |
| 3,983,903 A | * | 10/1976 | Kuehn, Jr. | F16L 55/02718 138/40 |
| 4,328,972 A | * | 5/1982 | Albertson | F16J 15/3208 264/138 |
| D286,807 S | * | 11/1986 | Paige | D23/249 |
| 4,706,663 A | * | 11/1987 | Makiej | A61M 15/00 128/200.18 |
| 4,910,739 A | * | 3/1990 | Sheng | G02B 5/005 359/227 |
| 4,941,244 A | * | 7/1990 | Ortmann | F42B 14/061 102/521 |
| 4,997,113 A | * | 3/1991 | Kirschner | B67D 1/0079 222/547 |
| 5,205,977 A | * | 4/1993 | Green | H01R 13/504 156/292 |
| 5,603,453 A | * | 2/1997 | Weaver | B05B 7/0075 239/419.3 |
| 6,405,944 B1 | * | 6/2002 | Benalikhoudja | A61L 9/145 128/200.18 |
| 6,467,137 B1 | * | 10/2002 | Kanda | B41J 2/161 156/252 |
| 6,520,767 B1 | * | 2/2003 | Ahern | F02M 25/0228 239/427 |
| 6,609,666 B1 | | 8/2003 | Blake | |
| 7,487,800 B2 | * | 2/2009 | Lammers | A61M 5/141 138/37 |
| 7,748,647 B2 | * | 7/2010 | Clerget | B05B 1/14 239/337 |
| 8,863,994 B2 | * | 10/2014 | Neuhaus | B05B 11/0027 222/402.13 |
| 8,950,435 B2 | * | 2/2015 | Lin | E03C 1/084 138/44 |
| 9,463,476 B2 | * | 10/2016 | Greiner-Perth | B05B 1/14 |
| 9,610,413 B2 | * | 4/2017 | Chen | A61M 15/0028 |
| 9,677,687 B2 | * | 6/2017 | Yli-Koski | F16L 55/02718 |
| 9,739,408 B2 | * | 8/2017 | Tecson | F16L 55/02718 |
| 9,855,571 B2 | * | 1/2018 | Camilleri | B01F 15/00512 |
| 10,022,773 B2 | * | 7/2018 | Rouns | B21D 51/02 |
| 2003/0178507 A1 | * | 9/2003 | Maria Rijn Van | A61M 15/00 239/337 |
| 2004/0074537 A1 | * | 4/2004 | Roots | B64D 13/00 137/487.5 |
| 2004/0164186 A1 | * | 8/2004 | Kladders | A61M 15/0065 239/543 |
| 2005/0194472 A1 | * | 9/2005 | Geser | B05B 1/00 239/602 |
| 2006/0213408 A1 | * | 9/2006 | Christ | B05B 1/14 111/200 |
| 2007/0157986 A1 | * | 7/2007 | Lammers | A61M 5/141 138/40 |
| 2007/0176028 A1 | * | 8/2007 | Laidler | B05B 1/3006 239/589 |
| 2008/0006719 A1 | * | 1/2008 | Clerget | B05B 1/14 239/337 |
| 2012/0206011 A1 | * | 8/2012 | Longoni | G21C 17/10 310/300 |
| 2013/0015259 A1 | * | 1/2013 | Kurasov | B29C 47/30 239/11 |
| 2014/0069737 A1 | * | 3/2014 | May | F01N 1/00 181/207 |
| 2014/0196535 A1 | * | 7/2014 | Sawchuk | G01F 15/00 73/272 R |
| 2014/0367490 A1 | * | 12/2014 | Neuhalfen | B05B 1/042 239/337 |
| 2015/0233493 A1 | * | 8/2015 | Irgens-Hagevik | F16L 55/02718 251/120 |
| 2015/0300525 A1 | * | 10/2015 | Lin | F16L 55/02718 181/247 |
| 2016/0192760 A1 | * | 7/2016 | Nishiura | A45D 19/02 239/337 |
| 2016/0208974 A1 | * | 7/2016 | Suganuma | F23K 5/00 |
| 2017/0056614 A1 | * | 3/2017 | Thuet | A61M 15/0025 |
| 2017/0130846 A1 | * | 5/2017 | Elliott | F16K 47/08 |
| 2017/0205015 A1 | * | 7/2017 | Tecson | F16L 55/02718 |
| 2017/0238605 A1 | * | 8/2017 | Matsumoto | A24F 47/00 |
| 2017/0281880 A1 | * | 10/2017 | Van Egmond | A61M 11/003 |

\* cited by examiner

AEROSOL OR SPRAY DEVICE, SPRAY NOZZLE UNIT AND METHOD OF MANUFACTURING THE SAME

CROSS-REFERENCE TO RELATED APPLICATIONS

This application is the National Stage of International Application No. PCT/NL2015/050455 filed Jun. 19, 2015, which claims the benefit of Netherlands Application No. NL 2013044, filed Jun. 20, 2014, the contents of which is incorporated by reference herein.

FIELD OF THE INVENTION

The invention describes a spray device for generation of a fine spray, a spray nozzle unit, comprising a spray nozzle plate and methods of manufacturing the same.

BACKGROUND OF THE INVENTION

Micro spray nozzle plates with orifices of a few micrometers or smaller, created by means of semiconductor manufacturing techniques, need to be packaged for connection to e.g. a spray pump or syringe according to pharmaceutical manufacturing protocols. Liquids, to be sprayed through spray nozzles with small orifices, often require the use of one, or a series of prefilter plates to prevent clogging of the spray orifices. It is known to make prefilter plates also by means of semiconductor manufacturing or micromachining. For medicinal or pharmaceutical purposes the use of glue, solvents or sealing agents, to mount a spray nozzle plate and/or a prefilter in a spray nozzle unit, is not preferable. Plastic materials to be used in spray nozzle units are typically medical grade plastics, which have an acceptable low extractables and leachables profile. Most medical grade plastics are thermoplastic materials, such as polyethylene (PE), polypropylene (PP), polyvinylchloride (PVC), polyetheretherketone (PEEK), cyclic olefin polymer (COP), poly sulfone (PS), polyoxymethylene (POM), polycarbonate (PC), or polyamid (PA) and may be applied as part of the primary package of a medicinal fluid. The spray nozzle unit therefore comprises a medical grade thermoplastic package holding the nozzle plate with one or more prefilter plates, and it further needs to be packaged according to pharmaceutical manufacturing protocols in a bioburden controlled Good Manufacturing Practice (GMP) environment. The spray nozzle unit would ideally be used in an aerosol or spray device where no preservative is added to the medicinal liquid. In that case a spray nozzle unit needs to function as an impenetrable barrier for microbes to prevent them from entering the container of the spray device via the nozzle plate side.

In operation the spray nozzle unit is subjected to high operating liquid pressures at varying temperatures and there is a risk of internal leakage and loss of bacterial integrity between the polymer parts of the package and the nozzle plate or the prefilter. Moreover, being able to handle high operating pressures it is important to ensure that the spray nozzle plate cannot come loose or even ejected, thereby potentially hitting a person using the device. Typical operating pressures for aerosol and spray devices lie between 1 and 50 Bar, with possibly higher peak pressures at start and end of the spraying mode.

SUMMARY OF THE INVENTION

It is an object of the invention to provide a spray device that is able to at least partially meet one or more of the above needs.

In order to achieve this goal, there is provided a spray device comprising a nozzle plate having an spray nozzle orifice, and a holder having a seat, the seat holding the nozzle plate, wherein the holder is made of a thermoplastic material and wherein the seat comprises a first rim, the first rim being formed of the thermoplastic material and being an integral part of the holder, the first rim sealingly engaging a downstream surface of the nozzle plate and extending along a circumferential edge of the downstream surface of the nozzle plate.

As the first rim sealingly engages a downstream surface of the nozzle plate and extends along a circumferential edge of the downstream surface of the nozzle plate, it operates as a sort of O-ring, whereby a force of the pressurized liquid in operation presses the nozzle plate against the rim so as so seal the nozzle plate thus prevent liquid from leaking around the nozzle plate.

Surprisingly it was found that when a specific polymer rim was present extending over the silicon nozzle plate at the exit (or downstream) side a good liquid tight bonding of the packaged nozzle plate in a broad work range with respect to temperature and pressure was obtained. When in use, liquid for generation of the spray is forced in the holder and presses against the nozzle plate, which in turn then presses against the rim. The liquid tight sealing rim according to the invention can probably best be compared with the seal of an O-ring on a flat surface. It is known in the art to use a thin rim on the downstream side to fixate mechanically the nozzle plate, however no specific measure is known to guarantee a good liquid tight seal without the use of glue, solvent or sealing agent. The term upstream and downstream here relate to a flow direction of the liquid through the spray device when in use. According to the invention the larger the operating pressure the larger the operating force that the nozzle plate will induce on this ‘O-ring’, herewith creating a good liquid tight seal.

The nozzle plate is provided with at least one opening, also referred to as orifice, spray orifice, spray nozzle orifice, or similar wording. In use, at an upstream side of the nozzle plate, a pressurized liquid is provided. As a result of the pressurizing of the liquid, spraying of the liquid through the spray nozzle orifice will take place. Depending on dimensioning (orifice size, pressure, liquid viscosity, etc.) a continuous stream or preferably—using a small orifice diameter) a sequence of small droplets will be sprayed. The holder may have any suitable form, such as for example a cup, a block, etc. Furthermore, the holder may be integral with a liquid reservoir to hold liquid from which the aerosol is to be generated, etc. The holder may be made of a thermoplastic material, such as a thermoplastic. The term thermoplastic is to be understood as a material which is solid at room or ambient temperature, and which obtains some degree of plasticity when the temperature is elevated. Upon decrease of the temperature, the thermoplastic material returns to the solid state again, whereby it retains a form as obtained at the elevated temperature. The thermoplastic material may for example be PE, PP, PVC, PEEK, COP, PS, POM, PA. The elevated temperature at which a plasticity increases may for example be 50 to 300° C. The nozzle plate may comprise a single orifice or a plurality of orifices, e.g. arranged in a pattern. The orifices may extend from one face of the orifice plate to the other, opposing face of the orifice plate, i.e. extend through the orifice plate. The orifice plate can be made from a metal or a ceramic material, e.g. a semiconductor, e.g. silicon.

The seat may be formed by an opening in the holder, or any other suitable recess in the holder. The seat may be open at 2 sides, i.e. extend through the holder or through a part thereof.

In this document, the terms spray device, spray nozzle, spray nozzle unit, aerosol generator all refer to a device that, when being provided with pressurized liquid at an upstream side thereof, generates at a downstream side thereof a spraying of the liquid via at least one orifice in the nozzle plate. The orifice may be referred to as an opening, The nozzle plate comprises one or more orifices and may accordingly also be referred to as an orifice plate or as a spray nozzle plate. The spray device may generate any spray, such as an aerosol. Accordingly, the spray device may be an aerosol generator.

The holder comprises a through opening extending from the upstream side to the downstream side, whereby the seat is provided in the opening and whereby the nozzle plate closing the opening by engagement with the rim in the seat (so that the one or more nozzle orifices form a sole discharging path for the liquid).

In an embodiment, a width of the first rim in a direction parallel to the downstream surface of the nozzle plate is at least 25% of a thickness of the nozzle plate.

It has been found that the rim should not be too broad; otherwise the operating force becomes distributed over a larger contact area between the rim and the nozzle plate.

Otherwise the rim should be not too small or too thin otherwise the structure becomes mechanically weak. Typically the extension of the rim over the nozzle plate should be at least 50 micrometer and preferably smaller than 250 micrometer. The width of the first rim, resp. the extension of the first rim may to be understood as an average width seen along a circumference of the first rim.

In an embodiment, the first rim extends over in total between 10% and 25% of a surface area of a downstream surface nozzle plate.

In an embodiment, in a direction perpendicular to the downstream surface of the nozzle plate, the first rim has a thickness of minimum 50% and maximum 250% of a thickness of the nozzle plate. The thickness is to be understood as a depth in a direction perpendicular to the surface of the nozzle plate.

The thickness of the rim should be at least 100 micrometer and maximum 500 micrometer. If the rim is too thick it becomes too rigid and it will lose its sealing properties. With these dimensions a good liquid tight sealing can be guaranteed. The exact dimensions of the rim of course do depend on the size and thickness of the nozzle plate. For a 1 mm×1 mm×0.2 mm nozzle plate typically the extension of the rim over the nozzle plate should be at least 25% of the thickness of the nozzle plate and the thickness of the rim should be at least 50% and maximum 250% of the thickness of the nozzle plate. The rim should moreover not obstruct the passage of the liquid jets or hamper the supply of air. Typically the cavity that is formed by the rim and the nozzle plate should have an aspect ratio (width/depth) larger than 1. This cavity may be tapered, rounded or chamfered to allow a smaller aspect ratio.

In an embodiment, the spray device further comprises an adapter having an inner surface that fittingly holds an outer surface of the holder. In an embodiment, a stiffness of the adapter exceeding a stiffness of the holder so as to promote a reduction of a deformation of the holder by pressurized liquid. In other embodiments, a stiffness of the adapter may be the same as a stiffness of the holder. According to the invention the spray nozzle unit, comprising a plastic package or holder and a spray nozzle plate with an upstream and downstream (exit) side is characterized in that a polymer rim is extending over the nozzle plate at the downstream side at least 50 micrometer and preferably less than 250 micrometer.

The spray nozzle unit is further characterized in that the extension of the rim over the spray nozzle plate at the downstream side has a thickness of at least 100 micrometer and maximum 500 micrometer.

With preference the spray nozzle unit will be placed in an adapter of a relatively stiff and tough material such as PEEK, POM or a metal that is able to counterbalance the pressure forces during operation on the spray nozzle unit. In particular the adapter further comprises an adapter rim to support the rim of the holder to strengthen the spray nozzle unit during operation and helps in the liquid tight sealing during operation. In other words, the adapter may comprise an adapter rim extending at a downstream side of the holder and substantially parallel to the downstream surface of the nozzle plate so as to support the first rim of the holder during operation. The dimensions of the support rim of the adapter extending over the rim of the holder should match with each other, characterized in that the length of the adapter rim is between 50% and 200% of the holder rim and the thickness is also between 50% and 200% of the holder rim. Accordingly, in an embodiment, a width of the adapter rim as seen in a direction along the downstream surface of the nozzle plate is between 50% and 200% of a width of the first rim of the holder. Further in an embodiment in a direction perpendicular to the downstream surface of the nozzle plate, the adapter rim has a thickness between 50% and 200% of the holder rim.

The spray nozzle unit can be tapered on the outside. This means that the spray nozzle unit has a conical fit in its surroundings. To prevent that the plastic holder can be inflated at higher pressures, leading to internal leakages between the nozzle plate and the plastic holder, this conical fit has an optimal range for the angle. The angle is here defined as the angle of the conical fit, measured towards the central axis of the spray nozzle unit.

If the angle is chosen very small e.g. 5 degrees, tolerances in the external diameter of the spray nozzle unit and the internal diameter of the surroundings will give a large placement tolerance in the direction of the central axis. Material flexibilities or plastic deformation due to relaxation will have the same effect. This makes that the angle can be chosen smaller for more rigid materials. If the angle is chosen very large, e.g. 45 degrees or larger, the force exerted by the liquid due to the operating pressure in the direction of the central axis is not being translated in a higher lateral force preventing inflation of the walls of the plastic holder, leading to internal leakages between the nozzle plate(s) and the plastic holder.

In one embodiment of the invention, the outer surface of the holder and the inner surface of the adapter both have a tapering section that tapers positive in a downstream direction, preferably a tapering angle being between 5° and 45° with respect to an orthogonal direction. Accordingly, the spray nozzle unit is conical shaped and is placed in a corresponding conical adapter. The tapering is positive in the downstream direction, and should be between 5° and 45°, and preferably between 10° and 20°. This way, during operation, inward forces are created, sealing also the side walls of the nozzle plate in the holder.

In an embodiment, at least part of the seat tapers towards a downstream end thereof, thereby providing additional support to the nozzle plate and the rim to withstand a force applied into the nozzle plate by pressurized liquid at the upstream side of the nozzle plate.

A second polymer rim extending over the upstream side of the nozzle plate will not necessarily help in sealing because the fluid presses equally hard on such an upstream rim as on the upstream side of the nozzle plate. The above mentioned 'O-ring' explanation will not be valid here. However it might help in mechanically locking the spray nozzle plate in the holder.

In an embodiment, the spray device further comprising a prefilter plate, the prefilter plate being placed in the holder at a distance from the nozzle plate and at an upstream side of the nozzle plate, the holder comprising a second rim, the second rim extending along and fitting along a circumferential edge of a downstream surface of the prefilter plate in between the nozzle and the prefilter plate. Surprisingly it has been found however that when a silicon based prefilter plate is placed in the package within a specific distance from the nozzle plate at the upstream side, enabling the presence of a polymer rim in between the nozzle plate and the prefilter plate a strong contribution to the liquid tight bonding of the packaged spray nozzle unit is found. It is thought that the presence of polymer in between the silicon spray nozzle plate and the first silicon prefilter plate also acts as a sealing rim according to the above mentioned 'O-ring' explanation. The larger the operating pressure on the upstream side of the prefilter the larger the operating force that the downstream side of the prefilter will induce on the polymer rim in between the prefilter and the nozzle plate. Likewise it has been found that this second rim should not be too broad; otherwise the operating force becomes distributed over a larger contact area between the second rim and the prefilter. Otherwise the second rim should be not too small or too thin otherwise the structure becomes mechanically weak. Typically the extension of the second rim over the prefilter should be at least 50% of the thickness of the prefilter and preferably smaller than 250% of the thickness of the prefilter. The thickness of the rim should be at least 50% and maximum 250% of the thickness of the prefilter, in particular with a thickness of minimum 100 and maximum 500 micrometer. Also if the second rim is too thick it becomes too rigid and it will lose its sealing properties, and also the total dead volume increases too much between the nozzle and prefilter plate.

With the second rim according to the invention a hermetically closed seal is obtained between the upstream side of the nozzle plate and the downstream side of the prefilter, herewith strongly contributing to the microbial integrity of the spray nozzle unit. As spray pores generally need to be micron sized to generate the desired droplet size, the nozzle plate generally does not prevent microbial ingrowth. The holes in the prefilter can be chosen smaller, for example 0.35 micron or 0.22 micron or even smaller, down to 0.1 micron. This way the prefilter becomes a barrier for microbial ingrowth into the device container. In that case it is essential that the prefilter's sides are sealed perfectly inside the plastic holder.

In an embodiment, the holder, at an upstream side of the prefilter plate comprises a fixation rim to fixate the prefilter plate in the holder A third rim according to a possible embodiment of the invention can be created at the upstream side of the prefilter plate, which helps in fixating the prefilter plate in the holder and improving the sealing between the plastic holder and the prefilter plate.

In an embodiment, at least one of the nozzle plate and the prefilter is provided with a coating having molecules with end groups that have a strong interaction with molecules of the holder. A good bonding between the polymer and the nozzle plate (and/or between the polymer and the prefilter plate(s)) is obtained according to the invention in that such a plate may be provided with a coating having molecules with end groups that have a strong interaction with the molecules of the polymer, e.g. a silane with apolar end groups for coupling silicon oxide/nitride surfaces to PP or another material.

In an embodiment, the at least one of the nozzle plate and the prefilter plate is provided with anisotropic locking features on the downstream or upstream surface thereof, the anisotropic locking features to mechanically anchor the at least one of the nozzle plate and the prefilter plate in the holder, preferably the anisotropic locking features having a width between 2 and 200 micrometer and a depth/width aspect ratio of at least 2, more preferably at least 5. Accordingly, another embodiment to obtain a good bonding with the polymer of the holder is characterized, in that the nozzle plate and/or prefilter plate are provided with anisotropic locking features on the downstream or upstream side of the plates around its edges to mechanically anchor the plates in the holder, in particular anisotropic locking features with a width between 2 and 20 micrometer and a depth/width aspect ratio of at least 2, and with preference at least 5.

An embodiment to guarantee bacterial integrity is characterized, in that a first, second or third prefilter plate is present with a pore size less than 450 nanometer, in particular 220 nanometer, or in particular 100 nanometer. Accordingly, in an embodiment, the prefilter plate has a pore size less than 450 nanometer, in particular 220 nanometer, or in particular 100 nanometer.

In order to extend the operating temperature range of the spray nozzle unit, an embodiment of the invention is further characterized in that the polymer has a lowered temperature expansion coefficient, such as 5×10-5° C. or less.

In order to meet GMP manufacturing protocols the spray nozzle unit is further characterized in that all different components have at least one track and trace feature.

In an embodiment, the spray device comprises an identification feature having a dimension between 0.01 and 10 microns, the identification feature being identifiable with microscopy or fluorescence methods. In order to combat counterfeiting the spray nozzle unit is further characterized in that it has at least one hidden identification feature that has a dimension between 0.01 and 10 microns, that can be identified with microscopy of fluorescence methods. In an embodiment, the prefilter comprises a plurality of pores, wherein at least one of the pores of the prefilter has a different size than the remaining pores, preferably about 10-50 nanometer smaller or larger than the other pores, a location of the at least one of the pore having the different size providing the identification feature. For example at least one of the pores in the silicon prefilter has a different size in particular about 10-50 nanometer smaller or larger than the other pores, and the location of that pore is encrypted with a code on the same prefilter plate.

With preference a method for manufacturing a spray nozzle unit is used characterized in that the components are placed in a polymer package with a thermoplastic deformation process. In particular, the method for manufacturing a spray device in accordance with an aspect of the invention, as described below, may be used.

The spray device, in one or more of the described embodiments thereof, may for example be applied in a Good Manufacturing Practice (GMP) compatible spray nozzle unit, The spray device may comprise a polymer package with an acceptable leachables and extractables profile, a spray nozzle plate and one or more prefilters, that withstands a high operating spray pressure in a broad temperature range. In the prior art, the liquid tight bonding or molding of a micromachined silicon based nozzle or prefilter plate to a pharmaceutical grade thermoplastic material is strongly hampered by the low adhesion between the materials, the deformability and relaxation of the thermoplastic under mechanical pressure, and the large difference in temperature expansion of the plastic and the silicon. These problems may be addressed in accordance with the various embodiments of the spray device as described above. In order to come to the present invention, several designs and sealing strategies have been performed, also with different thermoplastic materials with different molding techniques such as injection molding, overmolding, and hot welding methods.

The invention is further based on a method for assembling a nozzle plate into a thermoplastic holder, while controlling the temperature of the nozzle plate and/or the holder.

According to an aspect of the invention, there is provided a method for manufacturing a spray device, the method comprising:
providing a nozzle plate and a thermoplastic holder having a tapered seat, wherein a smallest cross section of the tapered seat is smaller than the nozzle plate, the method comprising:
heating the nozzle plate;
   pressing the nozzle plate into the tapered seat of the holder by bringing the nozzle plate towards a smallest side of the tapered seat, thereby thermoplastically deforming a wall of the tapered seat;
   forming a spray device from an assembly of the nozzle plate and the thermoplastic holder, whereas a widest side of the tapered seat is pointing towards a supply side of the liquid.

Accordingly, a tapered seat is provided in the thermoplastic holder. At least one nozzle plate is provided, wherein a smallest cross section of the tapered seat is smaller than the nozzle plate. The nozzle plate and/or the holder are heated, followed by pressing the nozzle plate into the holder by bringing this nozzle plate towards the smallest side of the tapered seat, thereby thermoplastically deforming the seat wall. This forms a spray device from the nozzle plate with holder, whereas the widest side of the tapered seat is pointing towards the supply side of the liquid.

According to the invention, a dimension of the orifice plate exceeds a dimension of the seat at the intended position of the orifice plate in the seat. The intended position of the orifice plate is to be understood as the position at which the orifice plate is to be placed in the seat. The dimension of the orifice plate may be a length, width, diameter etc. of the orifice plate. The dimension of the seat may be a size of the seat measured at the location where the orifice plate is intended to be positioned. Thus, the dimension is to be understood as a dimension which is substantially perpendicular to a direction of insertion of the orifice plate into the seat when placing the orifice plate into the seat. As a result, the orifice plate is oversized in respect of the opening in the seat at the intended position of the orifice plate. The orifice plate is heated before placing it in the seat of the holder. Accordingly, the thermoplastic material of the holder will raise in temperature as the heated orifice plate contacts the thermoplastic material upon placing of the orifice plate in the seat. When the orifice plate is placed in the seat, the thermoplastic material of the seat, e.g. a wall of the seat, will be deformed as the orifice plate is oversized, causing the orifice plate to interact with the seat by e.g. scraping material from the wall of the seat, and/or pushing material from the wall of the seat forward in a direction of the placement of the orifice plate.

As a result of the deformation of the seat, the seat as deformed will enclose an outside edge of the orifice plate, thereby allowing compensation of larger tolerances in a dimension of the orifice plate. As the thermoplastic material tends to shrink upon cooling down, the material of the seat that encloses the outside edge of the orifice plate will form itself around the outside edge of the orifice plate, thereby sealing the orifice plate thus preventing a leakage of the liquid from which the aerosol is to be generated. Part of this tension will be creeping away. The creep process is influenced by the type of thermoplastic material and by storage time and temperature. However, the tension will never completely go down to zero and thus improve sealing. The deformation of the seat may also provide for a ridge of thermoplastic material at the edges of the orifice plate, in particular in front of the orifice plate in the direction of movement upon placement of the orifice plate in the seat. The deformation of the seat may even lead to a ridge just behind the orifice plate.

Thus, the orifice plate is being placed and leak free fixated in a single process step, without adding any glues or sealants.

The dimension may refer to a circumference, diameter, length and/or width: accordingly, the outer dimension of the orifice plate may be an outer circumference, diameter, length and/or width of the orifice plate and the inner dimension of the seat may be an inner circumference, diameter, length and/or width of the seat. Thereby, a sealing of the orifice plate around a circumference thereof may be provided by the circumferential edge of the orifice plate thermoplastically deforming the seat. Accordingly, a length and width of the orifice plate may exceed corresponding inner dimensions of the seat at the intended position of the orifice plate in the seat. The step of forming a spray device from the assembly of the nozzle plate and the thermoplastic holder may comprise: actively or passively cooling down the assembly after the deformation took place, placing the assembly in a holder, or any further suitable manufacturing step.

A pressure on the spray nozzle unit in use, applied from the supply side, works in the right direction to compress the seal between the nozzle plate and the holder even tighter during operation. The tapered configuration also prevents the nozzle plate from being pushed through the plastic, which release could potentially eject the nozzle plate at high speed with the possibility of personal injury.

Instead of the plastic housing parts being tapered like described before, or as additional feature, the sides of the nozzle plate can have locking features, e.g. being tapered as well, or having local protrusions. Potential embodiments thereof are being described in the drawings. Accordingly, the seat may have a constant cross sectional outline towards the discharging opening along at least part of a length of the seat from the inlet opening to the discharging opening. This may be beneficial for plastic injection moulding tooling for the thermoplastic holder.

To prevent the nozzle plate from coming loose when no spray pressure is applied, it is possible to locally heat and deform the widest side of the tapered seat to create a rivet-like flange or rim or rim behind the nozzle plate, as further illustrated in the drawings. Such a flange will also keep the nozzle plate in place during temperature cycles, causing thermal expansion, which may likely differ for the plastic holder and the nozzle plate.

Another potential embodiment of the invention comprises multiple nozzle plates, each with a different function in the liquid stream. The nozzle plate the closest to the outside world may function as a nozzle plate, generating the spray. The middle nozzle plate may serve as a last chance filter, featuring an abundance of small holes, e.g. half the diameter of the spray orifices in the nozzle plate. The third nozzle plate, closest to the supply side of the liquid, may serve as a prefilter, featuring an abundance of larger orifices, filtering larger particles out of the liquid. The nozzle plate closest to the outside world has the smallest surface area. The nozzle plate closest to the supply side of the liquid has the largest surface area. The nozzle plate and the middle nozzle plate are both kept in place by a rivet like flange or rim, creating by assembling the next nozzle plate or microsieve.

Such an embodiment of the invention comprises a method for manufacturing a spray device featuring two or more nozzle plates, wherein a first one of the nozzle plates has a smaller surface area than a second one of the nozzle plates, the method comprising: placing the first one of the nozzle plates in a seat of the thermoplastic holder, placing the second one of the nozzle plates under controlled temperature in the seat of the thermoplastic holder, the thermoplastic holder thereby being locally thermoplastically deformed into an (e.g. rivet-like) flange, thereby fixating the first one of the nozzle plates. The rim may thereby follow a surface of the nozzle chip. A diameter of the second one of the nozzle plates may be larger than a diameter of the seat in the holder, so as to scrape material from a wall of the holder to form the flange. Accordingly, two or more nozzle plates or microsieves are being placed into a plastic holder in a tapered stack. The nozzle plate which is placed first, has a smaller surface area than the last nozzle plate (closest to the supply side of the liquid). When placing the second nozzle plate at elevated temperature, the plastic holder is locally thermoplastically deformed and forms a rivet-like flange or rim or rim, securing the first nozzle plate. The rivet-like flange or rim or rim forms a tight seal against the surface of the first nozzle plate, perfectly following small imperfections in the surface.

Instead of using a subsequent nozzle plate to create the rivet-like flange or rim or rim by thermoplastically deforming the holder, a thermode can be used. A thermode is a heated object which may be cooled down and removed after forming the flange. Or alternatively a non-stick coating on this thermode makes the cooling down superfluous, allowing faster processing times.

The shape of the nozzle plates may be symmetrical (e.g. square, triangular, circular, hexagonal) or non-symmetrical (e.g. rectangular). The nozzle plate can be very small, e.g. for a square nozzle plate 1×1 mm, preferably 0.7×0.7 mm, more preferably 0.5×0.5 mm or even smaller.

Such a nozzle plate can be placed with a heated bond head. This makes that the nozzle plate melts its way into the thermoplastic holder, hence perfectly following the imperfections of the side surfaces of the nozzle plate. The tolerances of the seat in the plastic holder are less critical by using this heated bonding. The heated bond head temperature can be varied between 50 and 300° C. for different plastics with different melt temperatures. Accordingly, in an embodiment, the orifice plate is heated by an heated bond head, the placing the orifice plate into the seat of the holder being performed by the heated bond head. The aerosol generator may hence be manufactured using existing manufacturing devices, allowing to reliably and quickly scale up a manufacturing of the aerosol generator.

Heating the thermoplastic holder before placement of the nozzle plate and cooling it down after placement to room temperature, will improve sealing around the nozzle plate. Part of this tension will be creeping away. This relaxation process is being influenced by the type of thermoplastic material and by storage time and temperature. However, the tension will never completely go down to zero and thus improve sealing By means of this assembly method no glues or sealants are used, which is essential for primary packaging components for pharmaceutical applications. The described fabrication methods provide an ideal sealing, which cannot be penetrated by microbes.

The outside of the plastic holder may be conical. This way, when pressurizing the nozzle, the housing that holds the assembled nozzle plate, creates a resulting force inward during use, sealing the nozzle plate even more.

To fix the holding of the nozzle plate, a second object may be placed just behind it, as described before. For example a plastic part (e.g. a retainer ring) may be clicked in place, or a second nozzle plate or microsieve with e.g. one very large orifice can be placed with a heated bond head. This can e.g. also be a simple metal ring or a porous metal frit. The placement of such a second element creates a rivet like flange or rim that seals the first nozzle plate in its position, as illustrated in more detail in the drawings.

Heated placement of the second object creates a rivet like flange or rim that seals the first nozzle plate. Behind the second object, a second similar rivet like flange or rim may be created as described before, but this may not be necessary.

In a similar manner, three or more nozzle plates or microsieves may be placed into one holder. When using two (or more) nozzle plates or microsieves in one plastic holder, the nozzle plates may each have a different function. The tapered stack of nozzle plates or microsieves may be used for different filtration steps for the spray device or to prevent microbial ingrowth into the container.

The shape of the nozzle plates may be symmetrical (e.g. square, triangular, circular, hexagonal) or non-symmetrical (e.g. rectangular). If the shape is not center point symmetric, an angled stack may be formed without increasing the size of each subsequent nozzle plates, but resulting in creating rivet-like flange or rim in an equal manner. The nozzle plate which has the largest pressure drop, the spray nozzle plate that sprays into the outside world, typically has the smallest size and is the strongest.

An example: when using two nozzle plates, the second one, placed just behind the first nozzle plate, the spray nozzle plate with the spray orifices towards the outside world, may be a nozzle plate with a micro sieve function. Sealing off such a second nozzle plate with a second rivet like flange or rim (or a subsequent nozzle plate) may be especially desired in case this micro sieve nozzle plate forms an anti-microbial barrier from the outside world towards the sterile container content. The micro sieve may be equipped with small pores, smaller than 1 µm, smaller than 0.45 µm, smaller than 0.33 µm or even smaller than 0.22 µm to prevent microbial ingrowth through the spray device into the device's fluid container.

In an embodiment, at least 3 orifice plates are placed in the holder, the at least 3 orifice plates forming a stack The stack may e.g. provide a pre filter, a last chance filter and a spray nozzle Having three nozzle plates in the liquid path may be beneficial for the filtering strategy: e.g. a 5 µm prefilter micro sieve, then a 1 µm last chance filter micro sieve and then a nozzle nozzle plate with 2 µm pores. The pre filter filters large contamination particles thus avoiding them to reach the last chance filter and the nozzle. The last chance filter removes small contamination particles thus preventing a clogging of the spray nozzle.

This assembly method makes it possible to choose an optimal manufacturing process for each function. The thickness of the nozzle plates may be varying per function of the plate in the stack. It may e.g. also be used to make a triple nozzle plate stack fit in the same plastic holder as used for a double nozzle plate stack. The first nozzle plate may be the strongest one and may be made from another material than the micro sieve nozzle plates in the stack. The membrane surface of a nozzle plate with a micro sieve function can be chosen as large as possible, to provide the maximum sieve surface and sieve capacity. The membrane(s) of the nozzle plate can be chosen much smaller, to optimize strength. A micro sieve nozzle plate may have optimally enlarged sieve surface, e.g. by introducing pillars or other 2 or 3 dimensional micro-structures. Surfaces of different nozzle plates may be smooth or very rough if desirable.

Between the nozzle plates cavities are formed in the assembled spray device. These cavities may contain an anti-microbial coating or an anti-microbial material depot may be assembled in this cavity in between two nozzle plates. Using a plastic material with anti microbial additives for the plastic holder will also result in the availability of an anti microbial agent in between the nozzle plates.

One of the benefits of this way of assembling a spray device, is that the nozzle plates, e.g. silicon nozzle plates, can be coated on wafer scale. A coating deposited on the 'outside' of a wafer, in this assembly becomes the 'inside' of the cavity between two nozzle plates. Coated surfaces may end up on the outside of the aerosol generator or on the inside of a cavity between two orifice plates, or on the inside of the aerosol generator, facing the supply of liquid.

Each nozzle plate in an assembled spray device may have a different coating with a different function (e.g. anti-fouling or anti-microbial or ultra-hydrophobic on the outside of the nozzle plate, anti-microbial inside the cavity between two orifice plates) Coatings may be leaching (e.g. like silver, copper, other ion forming metals) or stationary (e.g. like QAS, quaternary ammonium salt or titanium dioxide coatings). Even a 'ink jet printed' coating of biologic or chemical origin (e.g. benzalkonium chloride) may be deposited on a wafer and by this assembly method become part of the inside of a cavity.

Nozzle plates can be single side coated or double side coated, in which case the coating ends up on an 'inside surface' and an 'outside surface' simultaneously.

Holes in the subsequent nozzle plates in the stack may be placed asymmetrically to influence the aspect ratio of the liquid path, e.g. to prevent microbial ingrowth. This way bacteria have to go a longer way in a narrow cavity from one series of orifices to the series of orifices in the next nozzle plate, whereas the cavity may contain an anti-microbial agent.

Other materials which otherwise may be difficult to assemble in a spray device may now be captured between two nozzle plates (or between a nozzle plate and a retainer ring, from metal, ceramic or another material). Herewith complex stacked sandwiches of materials can be made with filtering capabilities or anti-microbial properties. Also an antimicrobial material depot, e.g. a metal part or a porous frit (e.g. from an anti-microbial treated plastic, metal or ceramic) can be placed in the stack. Even a material that later slowly dissolves in the sprayed formulation, e.g. an anti-microbial agent, can be incorporated in the stack.

Additionally the spray device may be equipped with depth filters from a variety of materials, e.g. such as sintered porous plastic or non-woven paper filters.

The spray nozzle plate (the most downstream, the one closest to and spraying into the outside world) may be used to incorporate an over-pressure safety feature. E.g. a larger orifice which is covered by the plastic housing may be created as a well defined breaking point in the system. There a leak may be introduced at overpressure, reducing the risk that silicon fragments are launched towards the patient's eyes in case of an eye spray device or into the lungs, in case of an inhaler device.

In an embodiment, the nozzle plate comprises a metal or a ceramic material, such as silicon. Nozzle plates from micro machined silicon may be equipped with very small orifices, micron sized or even down to e.g. 0.22 micron or smaller, to create liquid passages which hold back bacteria.

In an embodiment, a method of manufacturing a spray device comprises
  providing an nozzle plate having a diameter;
  providing a thermoplastic holder having a seat, wherein the diameter of the nozzle plate exceeds a diameter of the seat at an intended position of the nozzle plate in the seat,
  heating at least one of the nozzle plate and the thermoplastic holder;
  placing the nozzle plate into the seat at the intended position, thereby providing a thermoplastic deformation of at least a part of the seat, and
  forming a spray nozzle unit from an assembly of the nozzle plate and the thermoplastic holder. Given the smaller initial dimension of the seat at the intended position of the nozzle plate, a thermoplastic deformation is provided that causes a shaping of the holder to hold and seal the nozzle plate.

In an embodiment, the nozzle plate is placed into the holder in a direction of movement of the nozzle plate relative to the holder, which direction corresponds to a flow direction of liquid from which the spray is to be generated in use of the spray device. After the thermoplastic deformation of the seat, a diameter of the seat upstream of the nozzle plate may exceed a diameter of the sear of the holder downstream of the nozzle plate. The smaller diameter at the downstream side may be provided by the insertion of the nozzle plate forcing thermoplastically softened material from the wall of the seat to be pushed forward (when inserting the nozzle plate from the upstream direction), possibly in combination with the seat having a tapered form narrowing in downstream direction. The term upstream and downstream relate to a flow direction of the liquid through the aerosol generator when in use. When in use, liquid for generation of the aerosol is forced in the holder and presses against the orifice plate, the smaller diameter of the seat of the holder upstream of the orifice plate holds the orifice plate against a pressure applied by the liquid.

According to a further aspect of the invention, there is provided an aerosol generator manufactured according to the method according to the invention. The aerosol generator may for example be configured to generate an aerosol from a medicinal fluid. The aerosol generator may also be used for non medical applications, such as e.g. household sprays, semiconductor cleaning machines, perfume and beauty care sprays.

According to a further aspect of the invention, there is provided a liquid administration device for spraying a liquid, the administration device comprising
a container for holding the liquid,
the spray device according to the invention or the spray device manufactured according to the method of the invention, and
a pressurizing device for propagating the liquid under pressure from the container to the spray device.

The liquid comprises a substantially sterile liquid, whereby the good sealing properties and reduction of bacterial ingrowth tend to keep the liquid sterile. The liquid may comprise a medicinal liquid.

It is noted that, although some of the embodiments are described in the context of the spray device according to the invention or in the context of the method of manufacturing according to the invention, the features and effects as described with reference to the method according to the invention may apply to the spray device according to the invention and vice versa.

The method according to the invention may be applied to manufacture the spray device according to the invention. The rim of the holder which fits a downstream edge of the nozzle plate may accordingly be provided by the method step of the thermoplastic deformation of the seat. Accordingly, the rim may also be referred to as a protrusion.

BRIEF DESCRIPTION OF THE DRAWINGS

Further embodiments, features and effects will follow from the appended drawings and corresponding description, in which non-limiting embodiments are disclosed, where:

FIG. 8b depicts a cross sectional view of an assembly of orifice plate and holder, making use of an orifice plate as depicted in FIG. 8a;

DETAILED DESCRIPTION OF THE INVENTION

Figure 1:
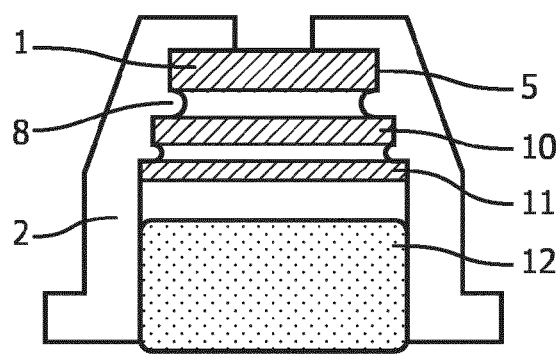
FIG. 1 depicts a cross sectional view of an assembly of orifice plates and holder according to an aspect of the invention, for use in an aerosol generator or other spraying device.

FIG. 1 shows a part of an aerosol generator according to a potential embodiment of the invention with three orifice plates (1, 10 and 11) and a sintered porous plastic pre filter (12). A spray nozzle orifice plate (1) is mounted in a thermoplastic holder (2). A second orifice plate (10) and a third orifice plate (11) are being mounted with heat and pressure, thus locally thermoplastically deforming the tapered seat wall (5), creating rivet-like flanges (8). These two orifice plates form a last chance filter (orifice plate 10), preferably with orifices which are half the diameter of the spray pore diameter in the spray nozzle orifice plate (1), and a pre filter (orifice plate 11) with larger orifices than the last chance filter. A sintered porous plastic pre filter (depth filter 12) is mounted and is being kept in place by a simple press fit.

Figure 2:
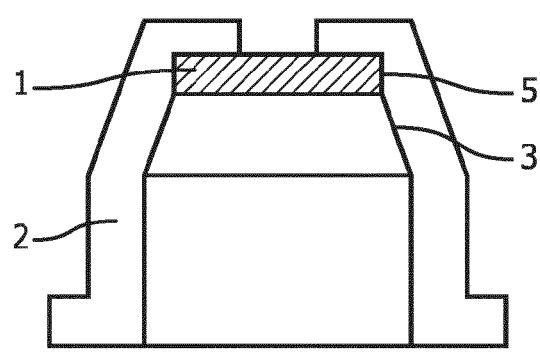
FIGS. 2, 3a, 3b, 4, 5a-5c, 6 and 7 depict a cross sectional view of various possible stages of fabrication of the assembly according to FIG. 1.

FIG. 2 shows an embodiment of the invention with one orifice plate (1) mounted in a thermoplastic holder (2). The holder (2) is provided with an originally tapered seat (3). The seat tapers from an inlet opening (lower side opening of seat) to a discharging opening (upper side opening of seat). When inserting the orifice plate into the seat, the seat is locally thermoplastically deformed (5), which may tend to perfectly following the contours of the orifice plate (1). At the intended position of the orifice plate in the seat of the holder, i.e. at the position as depicted in FIG. 2, before inserting the orifice plate into the holder, thus before deforming the seat, the outer dimension of the orifice plate (e.g. the outer width, diameter or circumference) exceeds a corresponding inner dimension of the seat (e.g. the inner width, diameter or circumference) of the holder, causing the seat to thermoplastically deform where it contacts the orifice plate when the heated orifice plate is inserted and establishes contact with and because of the orifice plate being over-dimensioned in respect of the seat, exerts a force onto the seat. The dimension of the orifice plate and seat are to be understood as dimensions in a direction substantially perpendicular to the direction of insertion (as indicated by the arrow in FIGS. 3a and 3b as will be described below).

Figure 3A:
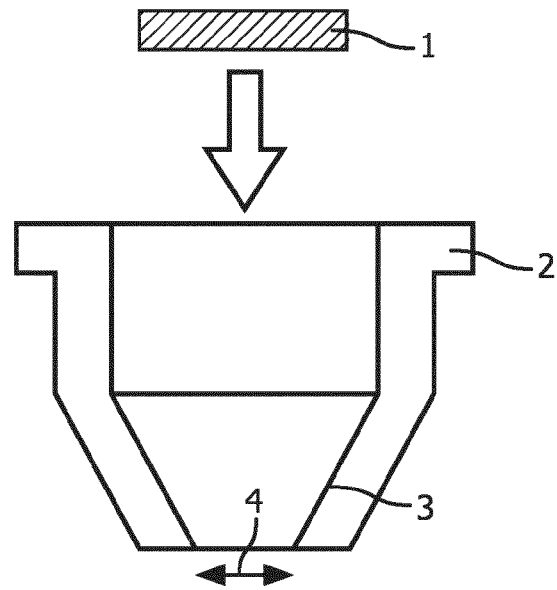

FIG. 3a shows a partly tapered seat (3) in a thermoplastic holder (2). An orifice plate (1) is provided, and inserted into the seat (a direction of insertion being indicated by the arrow in FIG. 3a), the insertion being performed in a direction of tapering of the seat, i.e. in a direction towards a discharging, outlet opening 4 of the seat which is smaller then the inlet opening. At the outlet opening, the smallest cross section of the tapered seat (3) is smaller than the orifice plate (1).

Figure 3B:
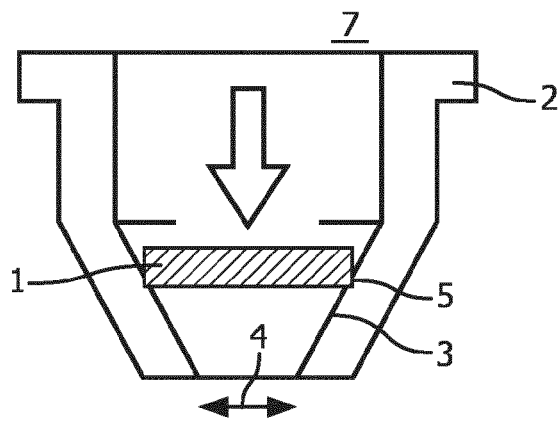

FIG. 3b shows that the orifice plate (1) after having been heated or while being heated, has been inserted into the seat followed by pressing the orifice plate (1) into the holder (2) by bringing the orifice plate (1) from the widest side (7) of the tapered seat (3) towards the smallest side (4) of the tapered seat (3), thereby thermoplastically deforming the seat wall (5). The direction of insertion is indicated by the arrow in FIG. 3b. This forms an aerosol generator from the orifice plate with holder, whereas the widest side (6) of the tapered seat is pointing towards the supply side of the liquid (7).

Figure 4:
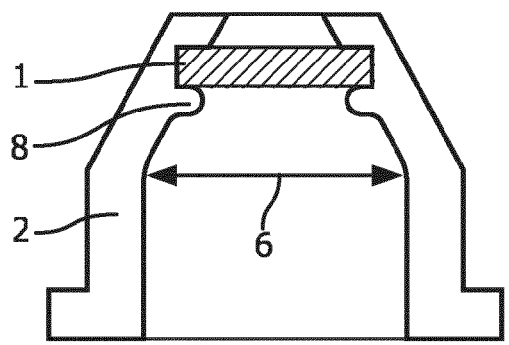

FIG. 4 shows another potential embodiment of the invention, where an orifice plate (1) is mounted in a thermoplastic holder (2). The orifice plate may have been mounted into the thermoplastic holder making use of the method as described with reference to FIGS. 2 and 3a-3b. As additional step may be performed as follows: By having locally heated and deformed the widest cross section (6) of the tapered seat, a rivet-like flange (8) has been created, which fixates the position of the orifice plate (1). The rivet like flange may be created by temporarily pushing (in the direction of insertion of the orifice plate) an object into the seat, the object having a size (e.g. diameter, circumference, length and/or width)

which exceeds that of the orifice plate, causing the seat to deform into the rivet like flange. The object may be heated so as to facilitate the local thermoplastic deformation to form the flange. Alternatively, the object may be inserted after the mounting of the orifice plate while the thermoplastic material of the seat proximate to the orifice plate is still warm, and this still exhibits a degree of thermoplastic plasticity. A manufacturing of the aerosol generator as depicted in FIG. 4 is illustrated with reference to FIG. 5a-5c as described below.

Figure 5A:
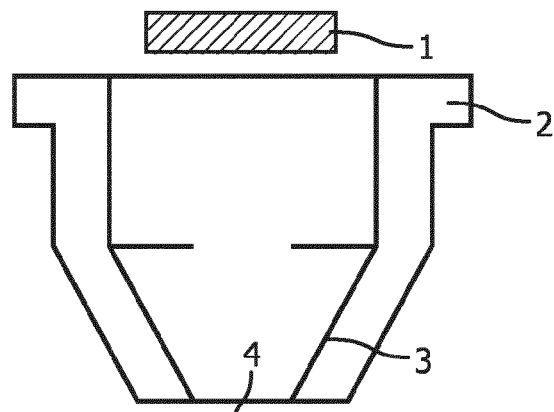

FIG. 5a shows a tapered seat (3) in a thermoplastic holder (2). An orifice plate (1) is provided, where the smallest cross section of the tapered seat (3) is smaller than the orifice plate (1). The orifice plate is heated before insertion or is inserted into the seat by a heated object, such as a heated bondhead (not shown FIG. 5a-5c.

Figure 5B:
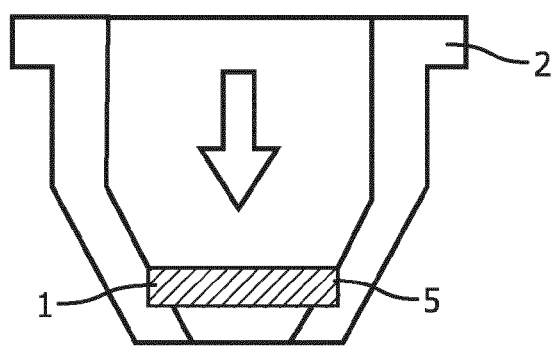

FIG. 5b shows the orifice plate (1) placed in the thermoplastic holder (2) in a direction as indicated by the depicted arrow. As the seat tapers toward a dimension that is smaller than the orifice plate, the orifice plate pushes against the tapering seat, thus locally plastically deforming the tapered seat wall (5)

Figure 5C:
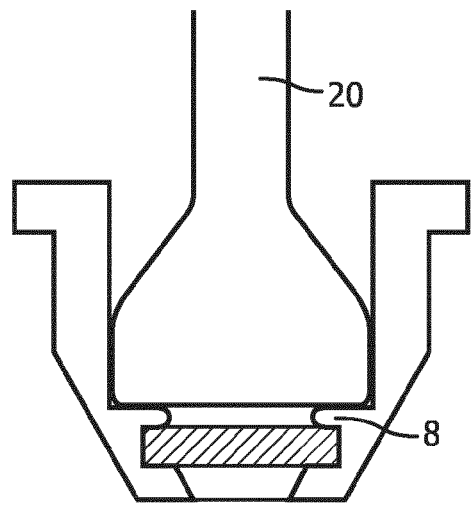

FIG. 5c shows the creation of the rivet-like flange (8) by using an object, such as in this example a thermode (20) to locally plastically deform the widest end (6) of the tapered seat. Thereto, the thermode is pushed into the seat in the direction of insertion. The thermode may be heated to promote local thermoplastic deformation of the seat.

Figure 6:
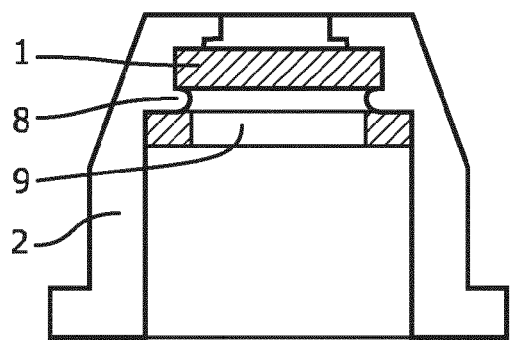

FIG. 6 shows a potential embodiment of the invention. An orifice plate (1) is mounted in a thermoplastic holder (2). A second object (9), in this case a metal ring shaped part, is placed just behind the first orifice plate (1), creating a rivet-like flange (8), to keep the orifice plate (1) fixated. The second object 9 may be mounted into the seat in a similar way as the insertion of the thermode as described with reference to FIG. 5c, whereby the second object is left in the seat and the thermoplastic material being allowed to cool down.

Figure 7A:
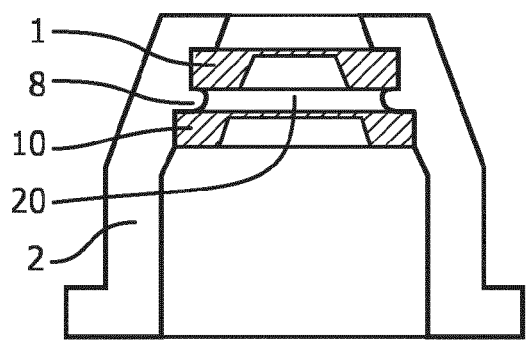
Figure 7B:
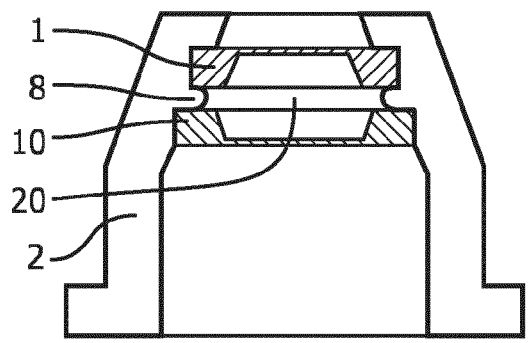

FIG. 7a shows a potential embodiment of the invention with two orifice plates. A first orifice plate (1), which has the function of spray nozzle orifice plate, is mounted in a thermoplastic holder (2). A second orifice plate (10), e.g. with a microsieve function, is being placed just behind the first orifice plate (1), creating a rivet like flange (8). The second orifice plate 10 may be mounted into the seat after having mounted the first orifice plate, whereby the second orifice plate is mounted in a similar way as the mounting of the first orifice plate. In order to again deform the seat while mounting the second orifice plate, the second orifice plate may be larger (in terms of e.g. diameter, circumference, length and/or width) then the first orifice plate. By the assembly method according to the invention a cavity (20) has been formed between the first and second orifice plates. The first and/r second orifice plate may be provided with a recess to form an area in the recess where a thickness of the orifice plate is reduced. The recess may be generated by any suitable technique. For example, in case the orifice plate is manufactured from a semiconductor material such as silicon, the recess may be etched into the orifice plate. In the part of the orifice plate where the thick ness is reduced, on or more openings may be provided to form orifices for generating an aerosol resp. to form a filter, FIG. 7b shows a potential embodiment with the same orifice plates, where the second orifice plate (10) has been mounted differently, thus creating a larger cavity (20). In FIG. 7a, the recesses in the first and second orifice plate are provided at a same (upstream) side, while in FIG. 7b, the recesses face each other, to form the larger cavity.

Figure 8A:
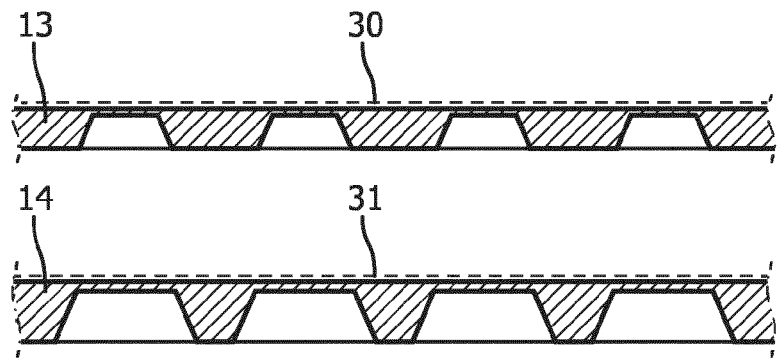
FIG. 8a depicts a cross sectional view of orifice plates.

FIG. 8a shows two silicon wafers. The first wafer (13) holds several hundreds of spray nozzle orifice plates (4 being depicted in FIG. 8a) and the second wafer (14) holds several hundreds of micro sieve orifice plates (4 being depicted in FIG. 8a). The first wafer is being coated on its top surface with an ultra hydrophobic coating (30). The second wafer is being coated on its top surface with an antimicrobial coating (31)

Figure 8B:
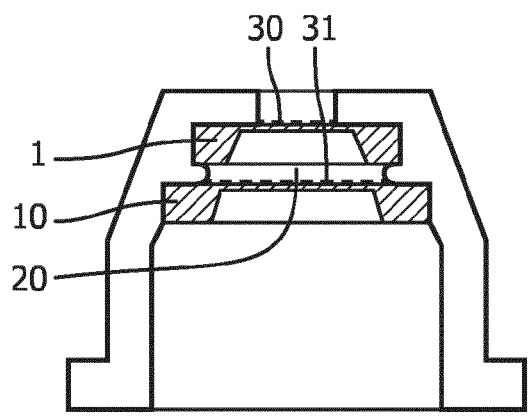

FIG. 8b shows an aerosol generator assembly, using orifice plates from the two silicon wafers described in FIG. 8a. The first orifice plate, the nozzle orifice plate (1), has the ultra hydrophobic coating (30) on the outside (i.e. on the downstream side). The second orifice plate, the microsieve plate (10) has an antimicrobial coating which now has ended up on the inside of the cavity (20).

Figure 9:
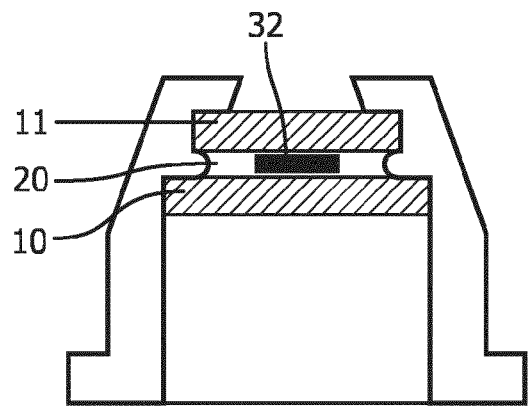
FIG. 9 depicts a cross sectional view of a assembly of orifice plates and holder according to another aspect of the invention, for use in an aerosol generator.

FIG. 9 shows a potential embodiment of the invention with two orifice plates plus a depot (32) of an anti microbial material, placed in the cavity (20) between the two orifice plates (10 & 11). The depot 32 may be formed by an absorbing structure which absorbs the anti microbial material, or may be formed by the anti microbial material itself.

Figure 10:
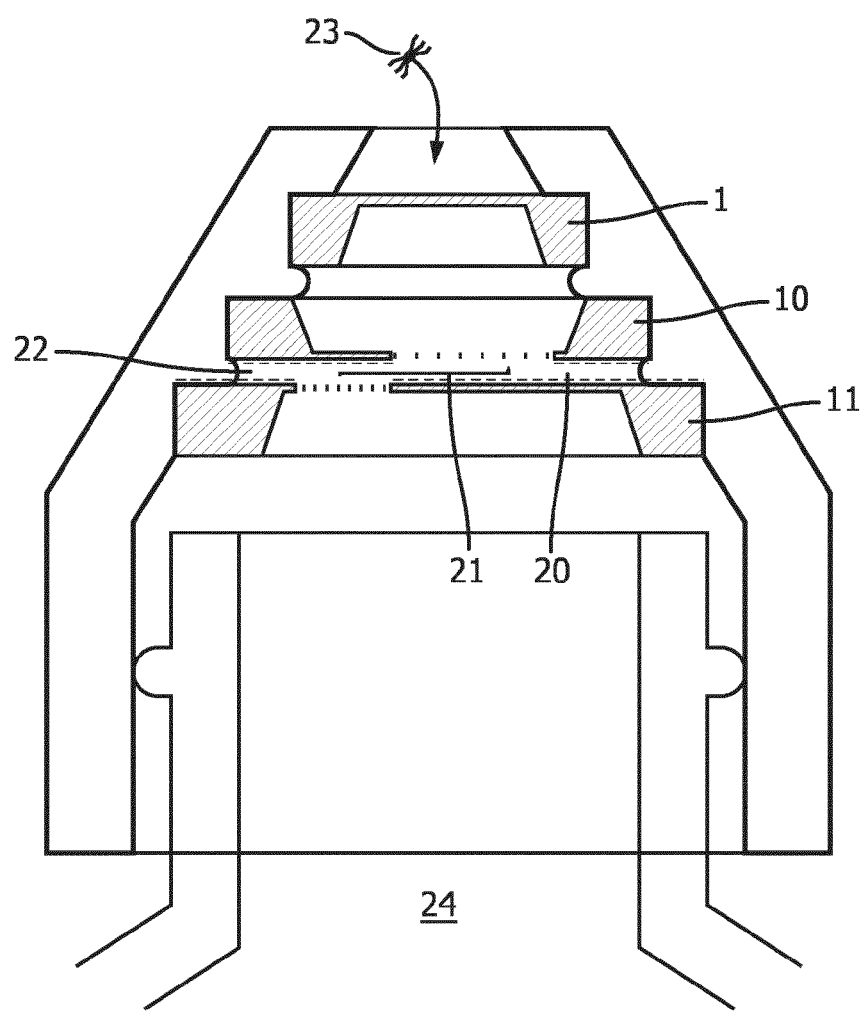
FIG. 10 depicts a cross sectional view of a assembly of orifice plates and holder according to another aspect of the invention, for use in an aerosol generator.

FIG. 10 shows a potential embodiment of the invention with three orifice plates. The spray nozzle orifice plate (1) faces the outside world at the downstream side of the aerosol generator. The hole pattern in the second orifice plate, a micro sieve plate (10) is placed asymmetrically in respect of a central axis of the holder extending from the inlet to the discharging opening. The hole pattern in the third orifice plate, also a micro sieve plate (11) is also placed asymmetrically on the other side, i.e. on the other side in respect of the central axis. This way the cavity (20) and the liquid path (21) between the two groups of micro sieve orifices has become very long and narrow, as it extends form the orifices in the third orifice plate which are located at the left side in the drawing of FIG. 10, while the orifices in the second orifice plate are located at the right side in the drawing of FIG. 10. The cavity has further been narrowed in that the recessed in the second and third orifice plates face away from each other casing the thin parts of the orifice plate to be closer together to form a more narrow gad there between. An anti microbial coating (22), applied on both micro sieve chips (10 & 11) prevents bacteria (23) from growing into the container (24) of the device. The container, of which only a part is depicted in FIG. 10, holds the liquid from which the aerosol is to be generated.

Figure 11A:
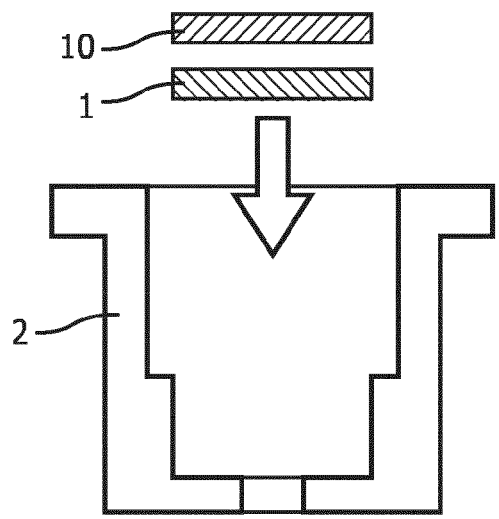
FIGS. 11a-11c depicts a cross sectional view of various possible stages of fabrication of a assembly of orifice plates and holder according to another aspect of the invention, for use in an aerosol generator.

FIG. 11a shows a thermoplastic holder (2). Two orifice plates (1) and 10 are provided, where the smallest cross section of the tapered seat (3) is smaller than the orifice plate (1). In contrast to the seats as depicted in and described with reference to FIGS. 1-10, the seat in the embodiment as depicted in FIG. 11 tapers stepwise instead of continuously. The first and second orifice plates 1 and 10 are placed into the seat by inserting them in the direction of the arrow in FIG. 11a. The first and second orifice plate may or may not be heated and may—but do not necessarily need to cause thermoplastic deformation of the seat.

Figure 11B:
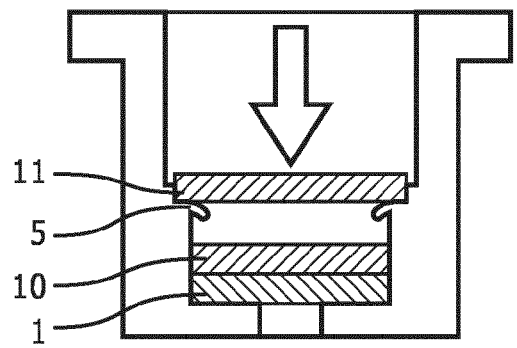

FIG. 11b shows the temperature controlled placement of a third orifice plate (11), locally thermoplastically deforming (5) the seat of the holder (2) by introducing the third orifice plate into the seat in the direction of the arrow (FIG. 11b). Part of the thermoplastical material of the holder is being scraped from a wall of the seat (5) in front of the third orifice plate (11) in order to form a flange at 5 between the second orifice plate and the third orifice plate.

Figure 11C:
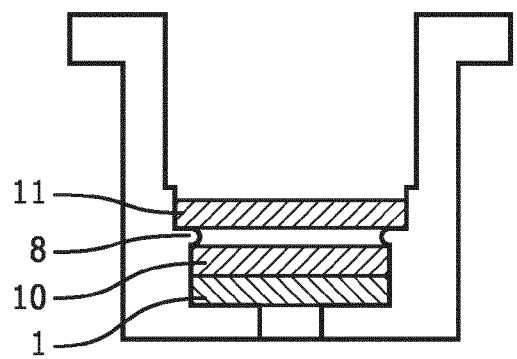

FIG. 11c shows a possible embodiment of an aerosol generator according to the invention as obtained by the placement of the orifice plates as described with reference to FIGS. 11a and 11b, where a first orifice plate (1), functioning as a spray nozzle orifice plate is provided and a second orifice plate (10), functioning as a last chance filter. The temperature controlled placement of a third orifice plate (11), functioning as a pre filter, has created a rivet like flange (8), fixating the first two orifice plates (1 and 10).

Figure 12:
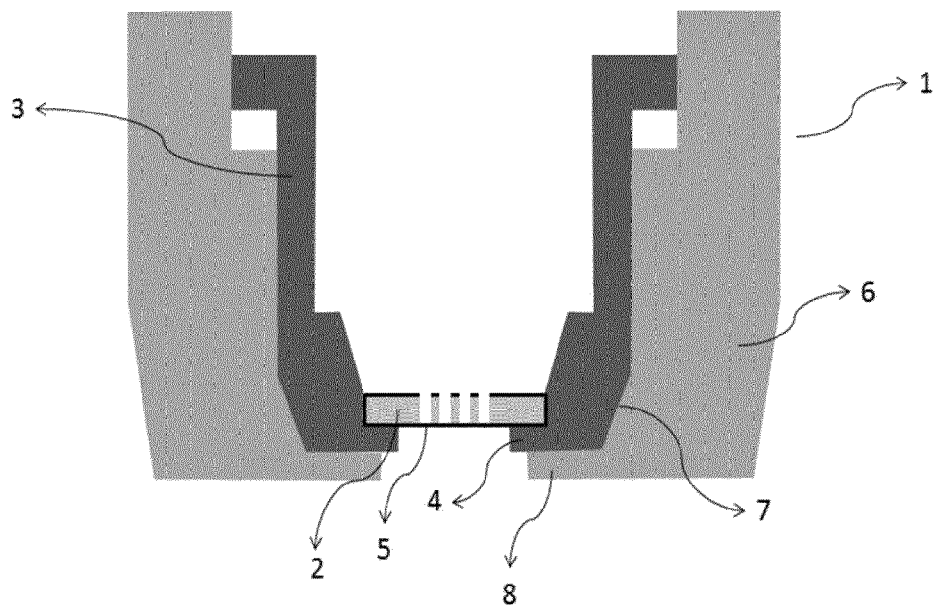
FIGS. 12-14 depict cross sectional views of spray devices in accordance with embodiments of the invention.

FIG. 12 shows an embodiment of a spray nozzle unit (1) with one nozzle plate (2) with a thickness of 200 um and a size of 1×1 mm. The nozzle plate (2) is made with silicon micromachining. For this a 200 um thick silicon wafer is used as a support and a 1 um thick silicon nitride layer for the provision of the nozzle orifices. The silicon nitride nozzle orifices are here 2 um in diameter. The spray nozzle nozzle plate (2) is mounted in a thermoplastic holder or package (3) of medical certified polypropylene that is characterized in having a rim (4) extending over the silicon nozzle nozzle plate at the exit or downstream side (5). The rim (4) extends horizontally over the nozzle plate (2) at the downstream side (5) with a length of 200 um and has a thickness of 200 um. The spray nozzle unit (1) further comprises an adapter (6) with a tapering section (7) to counterbalance thermal and pressure expansions of the thermoplastic holder (3). The adapter (6) may further comprise a support rim (8) to support the rim (4) of the holder (3) to strengthen the spray nozzle unit (1) during operation. Here the support rim (8) extends about 150 um and has a thickness of 200 um.

Figure 13:
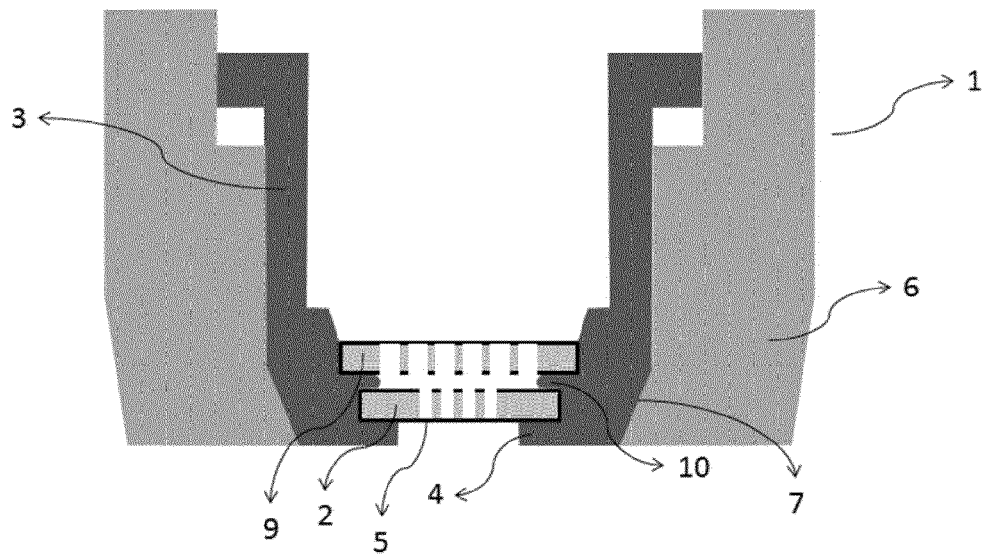
Figure 14:
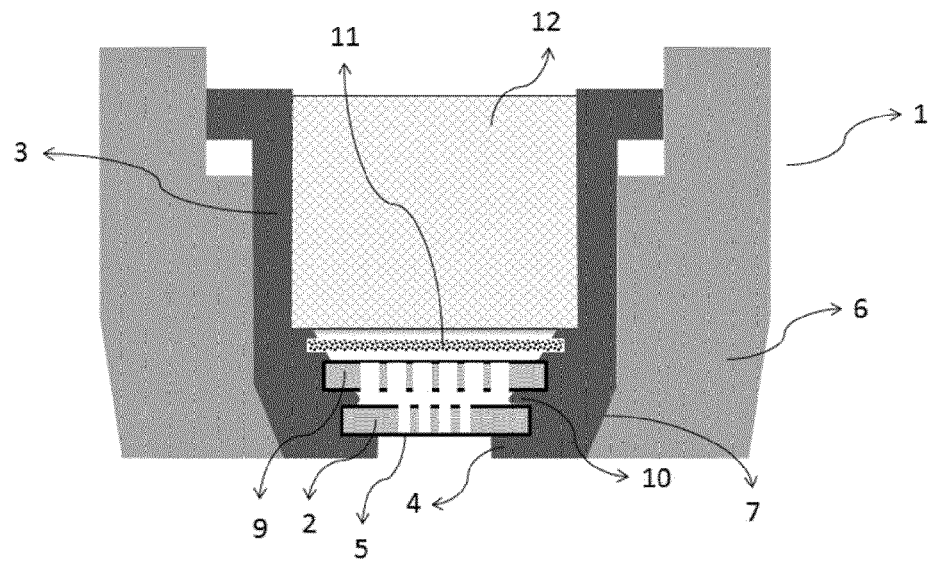
Figure 15:
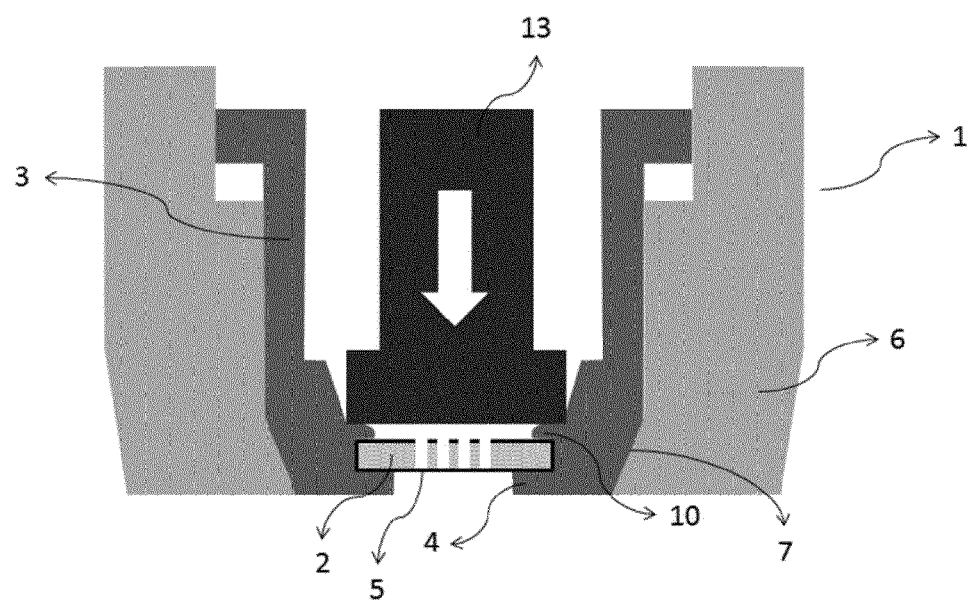
FIG. 15 depicts cross sectional view of a spray device in accordance with embodiments of the invention to illustrate a manufacturing of the spray device using a thermode.
Figure 16:
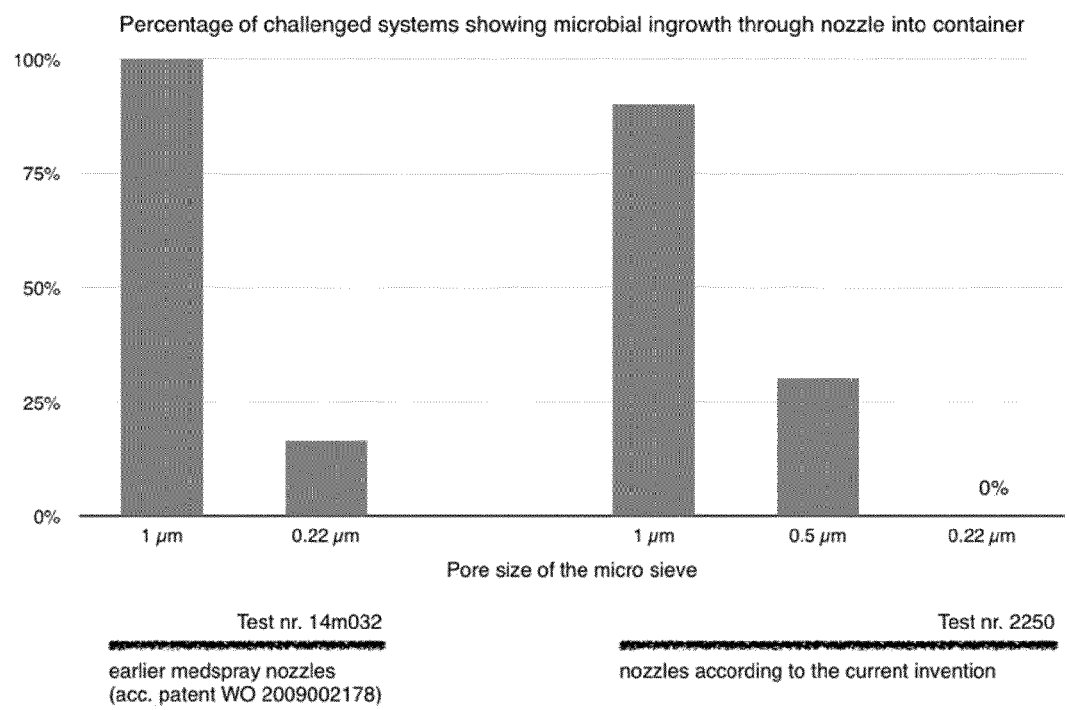
FIG. 16 shows a graph with microbial test results.
Figure 17:
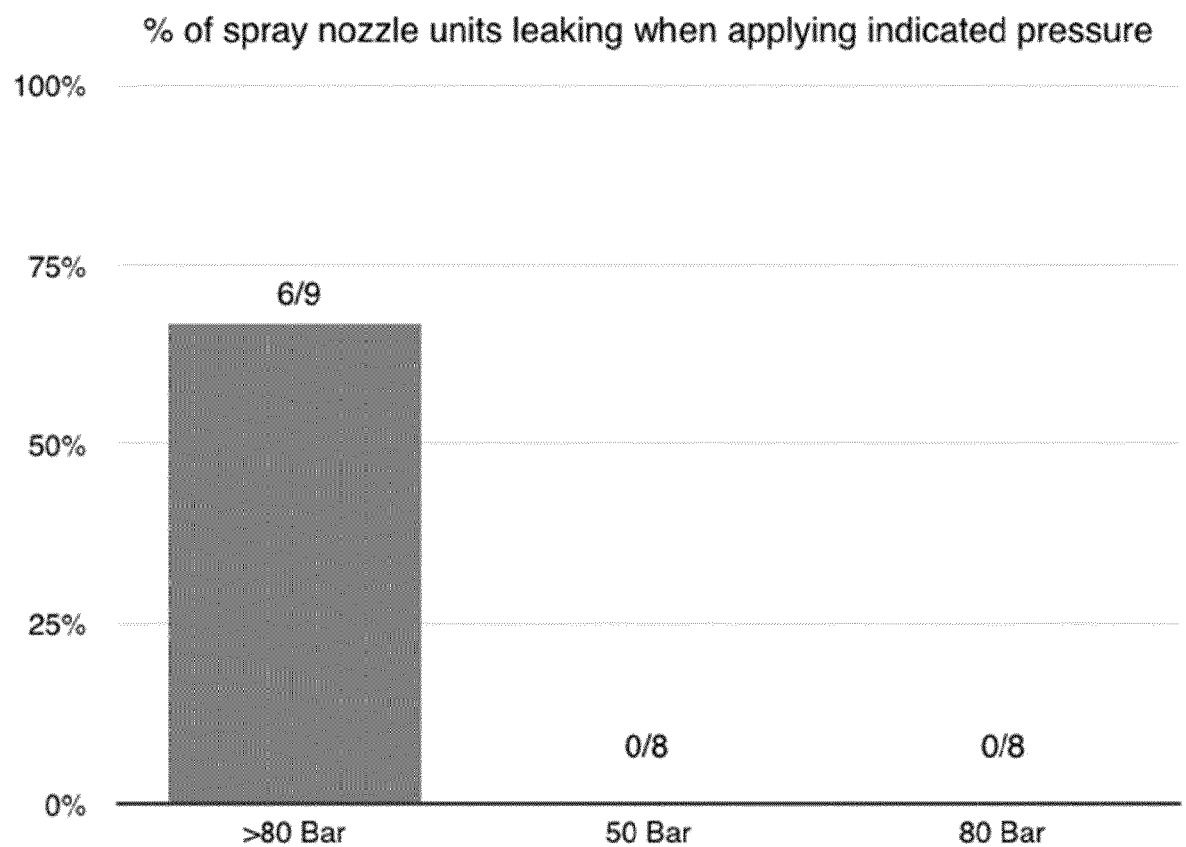
FIG. 17 explains an effect of a conical (tapering) fit.
Figure 17:
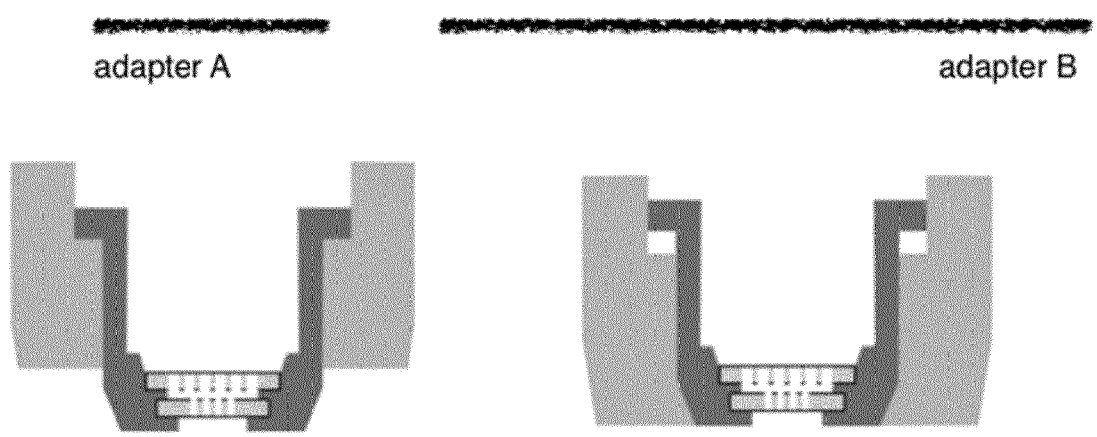
Figure 18:
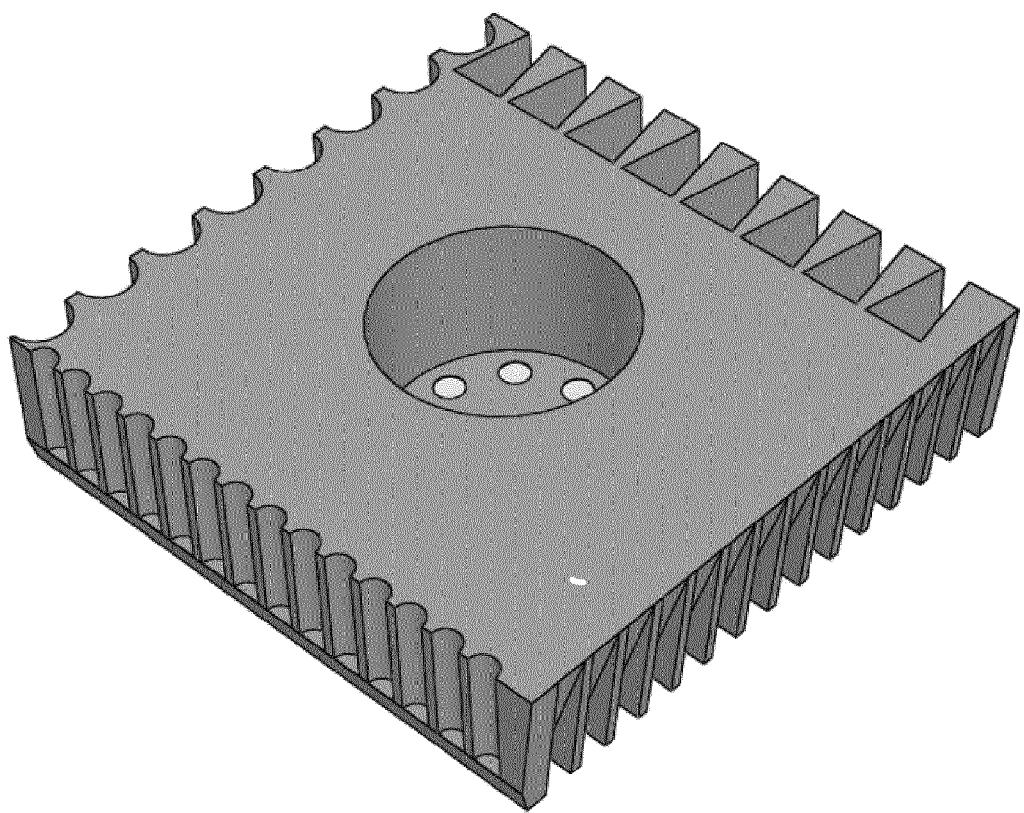
FIG. 18 depicts a schematic, perspective view of a nozzle plate comprising protrusions.

FIG. 13 shows an embodiment of a spray nozzle unit (1) with a nozzle plate (2), a thermoplastic holder (3) and a microsieve prefilter (9). The microsieve (9) is made with a silicon micromachining method similar as for making the nozzle plate (2) with a thickness of 200 um and has pores with a diameter of 0.45 um. In between the nozzle plate (2) and the prefilter (9) a second polymer rim (10) is present extending over the silicon nozzle nozzle plate (2) at the upstream side. Here the second polymer rim has a thickness of 100 um and extends with a length of 200 um. The membrane side of the microsieve (9) is here positioned on the upstream side of the spray nozzle unit (1), but can also be placed inverted.

FIG. 14 shows an embodiment of a spray nozzle unit (1) with a nozzle plate (2), a thermoplastic holder (3), a microsieve prefilter (9) and a sintered porous plastic prefilter (11), here with a pore size of approximately 10 um. Likewise a third filter (12) can be placed to collect particles from fluid at the upstream side.

FIG. 15 show a method for manufacturing a spray nozzle unit (1) with use of a thermode (13).

FIG. 16 shows a graph with microbial test results, comparing a single nozzle unit with a prefilter and a tapering adapter according to the current invention with a single nozzle unit without the use of a tapering adapter. The nozzles are challenged over a period of one week, then the content of the container with a nutrient solution is assessed for bacterial ingrowth.

The earlier nozzles unexpectedly show ingrowth with 0.22 microsieve pores, the new nozzles according to the invention do not, which indicates that the microsieve plates now are assembled in a way that perfectly seals them.

FIG. 17 shows the importance of a conical fit of the assembled spray nozzle unit in its surroundings. The plastic material used for the plastic holder used to generate this data, is polypropylene, the surrounding adapters A and B are made from a harder plastic (adapter A rapid prototyped polyamid, adapter B milled from polyoxymethylene). The graph shows that at higher pressures the polypropylene holder can be inflated, leading to internal leakages between the nozzle plate and the plastic holder.

FIG. 18 depicts a schematic, perspective view of a nozzle plate. Local protrusions are provided at each of the edges of the nozzle plate. Various protrusion profiles are depicted. For illustrative purposes, in order to illustrate different possibilities of the protrusion profiles, each edge of the depicted nozzle plate is provided with a different profile.

The invention claimed is:

1. A spray device having a spray nozzle unit, said spray nozzle unit comprising holder of thermoplastic material and a spray nozzle plate, wherein said spray nozzle plate comprises at least one spray nozzle orifice, wherein said holder comprises a recess that is open on opposite ends thereof and at least a portion of said recess tapers down towards a downstream end thereof, wherein said spray nozzle plate is fitted within said tapering portion of said recess, wherein said recess has a thermoplastic wall with a seat that holds said spray nozzle plate, wherein said seat comprises a first rim that sealingly engages a downstream surface of said spray nozzle plate and extends all along a circumferential edge of said downstream surface of said spray nozzle plate, wherein said seat comprises a second rim that engages an upstream surface of said spray nozzle plate and extends all along a circumferential edge of said upstream surface of said spray nozzle plate, wherein said spray nozzle plate has a lateral cross section in between a first lateral cross section of said seat at an upstream end and a second lateral cross section of said seat at a downstream end, wherein said first rim comprises a first thermally deformed portion of said thermoplastic wall of said recess, and wherein said second rim comprises a second thermally deformed portion of said thermoplastic wall of said recess.

2. The spray device according to claim 1, wherein the spray nozzle plate is a ceramic plate or metal plate.

3. The spray device according to claim 2, wherein the spray nozzle plate is a plate of semiconductor material, particularly of silicon.

4. The spray device according to claim 1, wherein said recess comprises a further seat that holds a filter plate having a plurality of filter openings, wherein said second rim sealingly engages a downstream surface of said filter plate and extends all along a circumferential edge of said downstream surface of said filter plate, wherein said further seat comprises a third rim that engages an upstream surface of said filter plate and extends all along a circumferential edge of said upstream surface of said filter plate, wherein said filter plate has a lateral cross section in between a first lateral cross section of said further seat at an upstream end and a second lateral cross section of said further seat at a downstream end, and wherein said third rim comprises a third thermally deformed portion of said thermoplastic wall of said recess.

5. The spray device according to claim 4, wherein the filter plate is a ceramic plate or metal plate.

6. The spray device according to claim 5, wherein the filter plate is a plate of semiconductor material, particularly of silicon.

7. The spray device according to claim 1, wherein a width of the first rim in a direction parallel to the downstream surface of the nozzle plate is at least 25% of a thickness of the nozzle plate.

8. The spray device according to claim 1, wherein, in a direction perpendicular to the downstream surface of the nozzle plate, the first rim has a thickness of minimum 50% and maximum 250% of a thickness of the nozzle plate.

9. The spray device according to claim 4, wherein in a direction perpendicular to the downstream surface of the spray nozzle plate, the second rim has a thickness of at least 50% and maximum 250% of a thickness of the filter plate, in particular with a thickness of minimum 100 and maximum 500 micrometer.

10. The spray device according to claim 4, further comprising a pre filter made of a sintered porous plastic material, mounted within said recess further upstream from the spray nozzle plate and the filter plate.

11. The spray device according to claim 1, further comprising an adapter having an inner surface that fittingly holds an outer surface of the holder, a stiffness of the adapter exceeding a stiffness of the holder.

12. The spray device according to claim 11, wherein the adapter comprises an adapter rim extending at a downstream side of the holder and substantially parallel to a downstream surface of the holder so as to support the holder during operation.

13. The spray device according to claim 11, wherein said outer surface of the holder abuts said inner surface of the adapter along a tapering section that tapers positive in a downstream direction at a tapering angle between 5 degrees and 45 degrees.

* * * * *